United States Patent [19]
Cook et al.

[11] Patent Number: 5,576,427
[45] Date of Patent: Nov. 19, 1996

[54] ACYCLIC NUCLEOSIDE ANALOGS AND OLIGONUCLEOTIDE SEQUENCES CONTAINING THEM

[75] Inventors: Philip D. Cook, Carlsbad, Calif.; Daniel J. Delecki, Radnor, Pa.; Charles Guinosso, Vista, Calif.

[73] Assignee: Sterling Winthrop, Inc., New York, N.Y.

[21] Appl. No.: 452,196

[22] Filed: May 26, 1995

Related U.S. Application Data

[63] Continuation of Ser. No. 40,326, Mar. 30, 1993, abandoned.
[51] Int. Cl.$^6$ .......................... C07H 21/04; C07H 21/02; C07D 473/34; C07D 473/18
[52] U.S. Cl. ...................... 536/23.1; 536/24.5; 536/24.3; 536/24.31; 536/24.32; 536/25.3; 544/276; 544/277
[58] Field of Search ............................ 514/44; 536/24.5, 536/24.3, 24.31, 24.32, 23.1, 25.3; 544/276, 277

[56] References Cited

PUBLICATIONS

P. Wanson et al., Cancer Res., vol. 51 (Aug. 1991) pp. 3996–4000.
E. Uhlmann et al., Chemical Reviews, vol. 90, No. 4 (Jun. 1990) pp. 543–584.
K. Augustyns et al., Nucl. Acids Res., vol. 19, No. 10 ('91) pp. 2587–2593.
J. Pitha, Adv. in Polymer Sci., (83) pp. 1–16, vol. 50.
K. Schneider et al., J. Am. Chem. Soc., vol. 112 ('90) pp. 453–455.
J. Holt, et al., Mol. Cell. Biol. (Feb. 1993) pp. 963–973.
G. Hoke et al., Nucl. Acids Res., vol. 19 #20 (91) pp. 5743–5748.
C. Stein et al., Science, vol. 261 (Aug. 1993) pp. 1004–1012.
B. Tseng et al., vol. 1 #1 (Mar. 1994) pp. 65–71.

*Primary Examiner*—Charles C. P. Rories
*Attorney, Agent, or Firm*—Paul E. Dupont; William J. Davis

[57] ABSTRACT

Compounds of formula I;

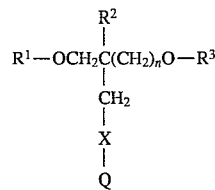

wherein
$R^1$ is hydrogen, or a blocking group that is compatible with oligonucleotide synthesis;
$R^2$ is hydrogen, nitro, lower alkyl amino, diloweralkyl amino or methyl;
$R^3$ is hydrogen or $-P(R^4)OR^5$;
$R^4$ is chlorine, 4-nitroimidazole, imidazole, tetrazole, triazole or di(lower-alkyl)amino-;
$R^5$ is methyl, 2-cyanoethyl or 2,2,2-trichloroethyl;
n is from 0 to 2
X is oxygen, sulfur, or $-NR^6$;
$R^6$ is hydrogen or lower alkyl;
Q is chosen from the group consisting of

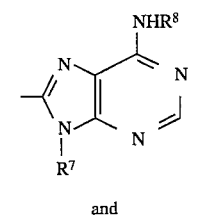

and

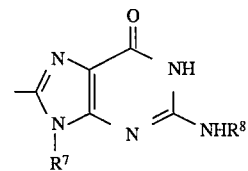

$R^7$ is lower-alkyl or loweralkyloxy methylene; and
$R^8$ is hydrogen, benzoyl, anisoyl, or lower-alkyl carbonyl and its pharmaceutically acceptable addition salts are nucleotide analogs. Modified oligonucleotides containing the nucleoside analogs of formula I are stable to nuclease degradation and are useful in inhibiting gene expression, in sequencing, and in mutagenesis.

8 Claims, No Drawings

ACYCLIC NUCLEOSIDE ANALOGS AND OLIGONUCLEOTIDE SEQUENCES CONTAINING THEM

CROSS-REFERENCES TO RELATED APPLICATIONS

This application is a continuation of application Ser. No. 08/040,326 filed on Mar. 30, 1993, now abandoned.

BACKGROUND OF THE INVENTION

The present invention relates to novel 1,ω-alkylenediol nucleoside analogs, to oligonucleotide sequences containing these analogs, to processes for preparing the nucleosides and the oligonucleotides incorporating them, to methods of using the modified oligonucleotides to inhibit nuclease degradation and gene expression, and to compositions containing the modified oligonucleotides.

Description of the Related Art

Schneider and Benner [*J. Am. Chem. Soc.* 112, 453–455 (1990)] disclose

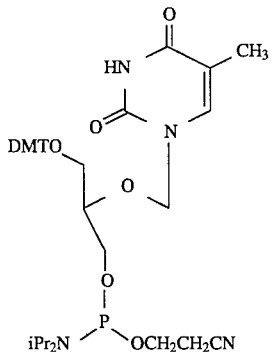

and oligonucleotide analogs containing this unit. The oligonucleotide analogs were hybridized with complementary natural oligonucleotides. The results were described by the authors as "disappointing for those hoping to use flexible oligonucleotide analogs as antisense compound". The replacement of even a single nucleoside in a nonamer resulted in a melting temperature depression of 12° to 15° in the duplex.

Prisbe et al. [*J. Med. Chem.* 29, 671–675 (1986)] disclose as antiviral agents:

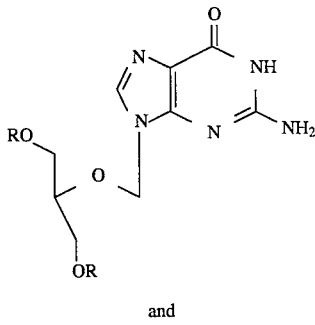

and

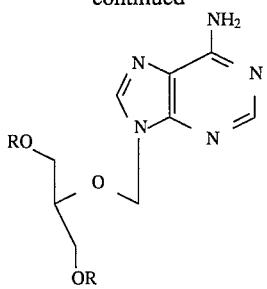

wherein R is hydrogen or a phosphate residue.

Harnden et al. U.S. Pat. No. 4,965,270 disclose as an antiviral 9-(3-hydroxy-2-hydroxymethylprop-1-oxy) guanine:

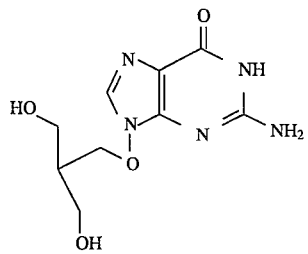

Schwartz and his colleages [*Science* 228, 585–587 (1985); *J. Molecular Evolution* 29, 284–287 (1989); J. Molecular Evolution 3–6 (1990)] describe the template directed homooligomerization of acyclic nucleotide analogs. The monomers have the formula

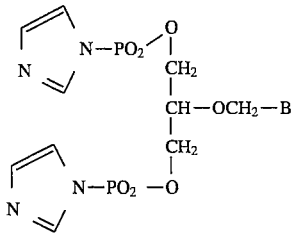

where B is cytosine, thymine, guanine or adenine.

Augustyns, et al *Nucleic Acids Research* 19 2587–93 (1991) discusses the influence of the incorporation of (S)-9-(3,4-dihydroxybutyl)adenine on the enzymatic stability and base pairing properties of oligodeoxynucleotides.

2. Field of the Invention

An antisense compound is a compound that binds to or hybridizes with a nucleotide sequence in a nucleic acid, RNA or DNA, to inhibit the function or synthesis of said nucleic acid. Because of their ability to hybridize with both RNA and DNA, antisense compounds can interfere with gene expression at the level of transcription, RNA processing or translation.

Antisense molecules can be designed and synthesized to prevent the transcription of specific genes to mRNA by hybridizing with genomic DNA and directly or indirectly inhibiting the action of RNA polymerase. A theoretical advantage of targeting DNA is that only small amounts of antisense compounds may be needed to achieve a therapeutic effect. Alternatively, antisense compounds can be designed and synthesized to hybridize with RNA to inhibit post-transcriptional modification (RNA processing) or protein synthesis (translation) mechanisms or affect mRNA stability. Exemplary target RNAs are messenger RNA (mRNA), transfer RNA (tRNA), ribosomal RNA (rRNA) heterogenous nuclear RNA (hnRNA) and the like. Examples of processing and translation mechanisms include splicing of pre-mRNA to remove introns, capping of the 5' terminus of mRNA, transport to the cytoplasm, hybridization arrest and Ribonuclease H mediated mRNA hydrolysis.

At the present time, however, the development of practical scientific and therapeutic applications of antisense technologies is hampered by a number of technical problems. Synthetic antisense molecules are susceptible to rapid degradation by nucleases that exist in target cells. The oligonucleotide sequences of antisense DNA or RNA, for example, are destroyed by exonucleases acting at either the 5' or 3' terminus of the nucleic acid. In addition, endonucleases can cleave the DNA or RNA at internal phosphodiester linkages between individual nucleotides. As a result of such cleavage, the effective half-life of administered antisense compounds is very short, necessitating the use of large, frequently administered, dosages.

Another problem is the extremely high cost of producing antisense DNA or RNA using available semiautomatic DNA synthesizers.

A further problem relates to the delivery of antisense agents to desired targets within the body and cell. Antisense agents targeted to genomic DNA must gain access to the nucleus (i.e. the agents must permeate the plasma and nuclear membrane). The need for increased membrane permeability (increased hydrophobicity) must be balanced, however, against the need for aqueous solubility (increased hydrophilicity in body fluid compartments such as the plasma and cell cytosol.

A still further problem relates to the stability of antisense agents whether free within the body or hybridized to target nucleic acids. Oligonucleotide sequences such as antisense DNA are susceptible to steric reconfiguration around chiral phosphorous centers.

Gene targeting via antisense agents is the predicted next step in human therapeutics [Armstrong, *Business Week* Mar. 5, 1990 p.88]. The successful application of antisense technology to the treatment of disease however, requires finding solutions to the problems set forth above.

One approach to preparing antisense compounds that are stable, nuclease resistant, inexpensive to produce and which can be delivered to and hybridize with nucleic acid targets throughout the body is to synthesize oligonucleotide sequences with modifications in the normal phosphate-sugar backbone structure and the point of attachment to the nucleotide base. This invention is directed to such an approach.

SUMMARY OF THE INVENTION

In a product aspect the invention relates to compounds of formula I

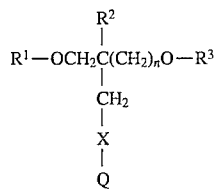

wherein $R^1$ is hydrogen or a blocking group that is compatible with oligonucleotide synthesis, such as methoxytrityl, or dimethoxytrityl; $R^2$ is hydrogen, nitro, lower alkyl amino, diloweralkyl amino or methyl; $R^3$ is hydrogen or $-P(R^4)OR^5$; $R^4$ is chloro, imidazolyl, 4-nitroimidazolyl, tetrazolyl, triazolyl or dilower-alkylamino preferably diisopropylamino; $R^5$ is methyl, 2,2,2-trichloroethyl or 2-cyanoethyl, preferably 2-cyanoethyl; X is oxygen, sulfur or $-NR^6-$, preferably oxygen; $R^6$ is hydrogen or lower-alkyl, preferably methyl; n is 0 to 2 and Q is a heterocyclic residue chosen from the group consisting of

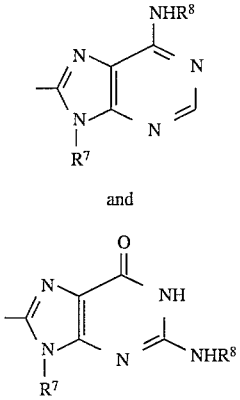

and wherein $R^7$ is lower-alkyl or loweralkyloxy methylene and $R^8$ is hydrogen, benzoyl, anisoyl or lower-alkylcarbonyl. The point of attachment of the heterocycle Q is at the 8-position carbon rather than the 9-position nitrogen as in naturally-occurring nucleosides.

In a further product aspect the invention relates to an oligonucleotide sequence of from about 6 to about 200 bases, preferably from about 12 to about 24 bases, most preferably about 15 bases, in which one or more nucleosides are replaced by a residue of formula V

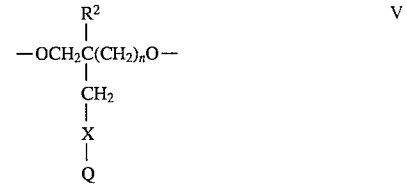

The compounds of formula I are useful as intermediates in the synthesis of the oligonucleotide sequences in which one or more residues are replaced. The oligonucleotide sequences are useful as antisense agents, for the inhibition of gene expression, in nucleic acid sequencing, diagnostic assays and for the inhibition of nuclease degradation.

For the purposes of the invention lower-alkyl means a hydrocarbon radical consisting of from about one to about four carbons in straight chains, branched or cyclic structures. Nucleoside and nucleotide have their standard meanings in the art: i.e. a nucleoside is a nucleoside base attached to a ribose or a 2-deoxyribose through the 9-position of the purine or the 1-position of the pyrimidine; a nucleotide is a 3' or 5' ribose-O-phosphate ester of a nucleoside. Nucleoside bases comprise uracil, thymine, cytosine, guanine, adenine and their variously modified and derivatized congeners as known in the art. Examples of such modified and derivatized bases include 5-fluorouracil, 5-bromouracil, 5-chlorouracil, 5-iodouracil, hypoxanthine, xanthine, 4-acetylcytosine, dihydrouracil, inosine, N6-isopentenyladenine, 1-methyladenine, 1-methylpseudouracil, 1-methylguanine, 1-methylinosine, 2,2-dimethylguanine, 2-methyladenine, 2-ethylguanine, 3-methylcytosine, 5-methylcytosine, N6-methyladenine, 7-methylguanine, 5-methylaminomethyluracil, 5-methoxyuracil, pseudouracil, queuosine, 2-thiocytosine, 5-methyl-2-thiouracil, 2-thiouracil, 4-thiouracil, 5-methyluracil, and 2,6-diaminopurine. The formulas and substituents retain the definitions initially assigned to them throughout the specification.

In a further composition aspect, the invention relates to compositions for inhibiting gene expression comprising the modified oligonucleotides described above and a pharmaceutically acceptable carrier.

In a method aspect, the invention relates to a method of inhibiting gene expression and to a method of inhibiting nuclease, particularly exonuclease, degradation of oligonucleotide sequences, which comprises providing a modified oligonucleotide described above.

In a process aspect, the invention pertains to processes for preparing compounds of formula II $$\begin{array}{c} R^2 \\ | \\ H-OCH_2C(CH_2)_nO-H \\ | \\ CH_2 \\ | \\ X \\ | \\ Q \end{array} \quad \text{II}$$

which comprises reacting a compound of formula III with a compound of formula IV

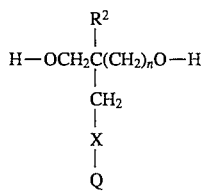

III $$Y-Q \quad \text{IV}$$

wherein Y is a leaving group readily displaced by a nucleophile and $R^9$ and $R^{10}$ are hydrogen, in which case the compounds of formula II are obtained directly, or protecting groups for a hydroxyl function, in which case the compounds of formula II are obtained by removal of the protecting groups by means known in the art. Preferred leaving groups, Y, are bromine, chlorine, iodine, toluenesulfonate, and methanesulfonate; most preferred is bromine. Preferred protecting groups are t-butyl, benzyl, phenyl or substituted phenyl or isopropylidene; most preferred is isopropylidene.

Compounds of formula III wherein n is 0–2 are commercially available, known in the art or belong to known families of compounds and can be obtained as pure enantiomers.

In a further process aspect the invention relates to a process for the synthesis of modified oligonucleotides in which a nucleoside is replaced by a residue of formula V

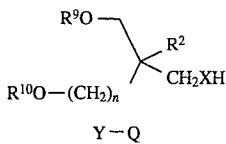

which comprises reacting an oligonucleotide sequence having one free 3' or 5' hydroxyl with a compound of formula VI

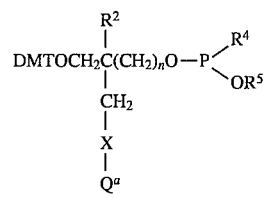

wherein DMT stands for the dimethoxytrityl residue and $Q^a$ is the subset of Q wherein $R^8$ is other than hydrogen ($R^{8a}$). Preferably $Q^a$ is

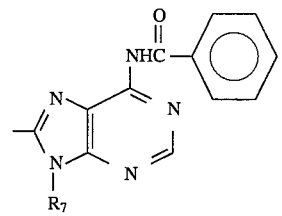

$Q^{a1}$ or

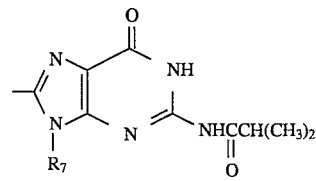

$Q^{a2}$

The oligomers wherein $R^8$ is hydrogen are then obtained from the corresponding $R^{8a}$ oligomers by deprotection using methods well-known in the art.

DETAILED DESCRIPTION INCLUSIVE OF PREFERRED EMBODIMENTS

Compounds of formula I may be synthesized by the route shown in scheme A:

SCHEME A

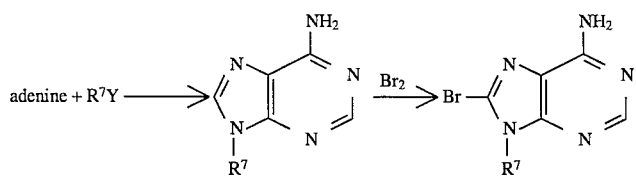

-continued
SCHEME A

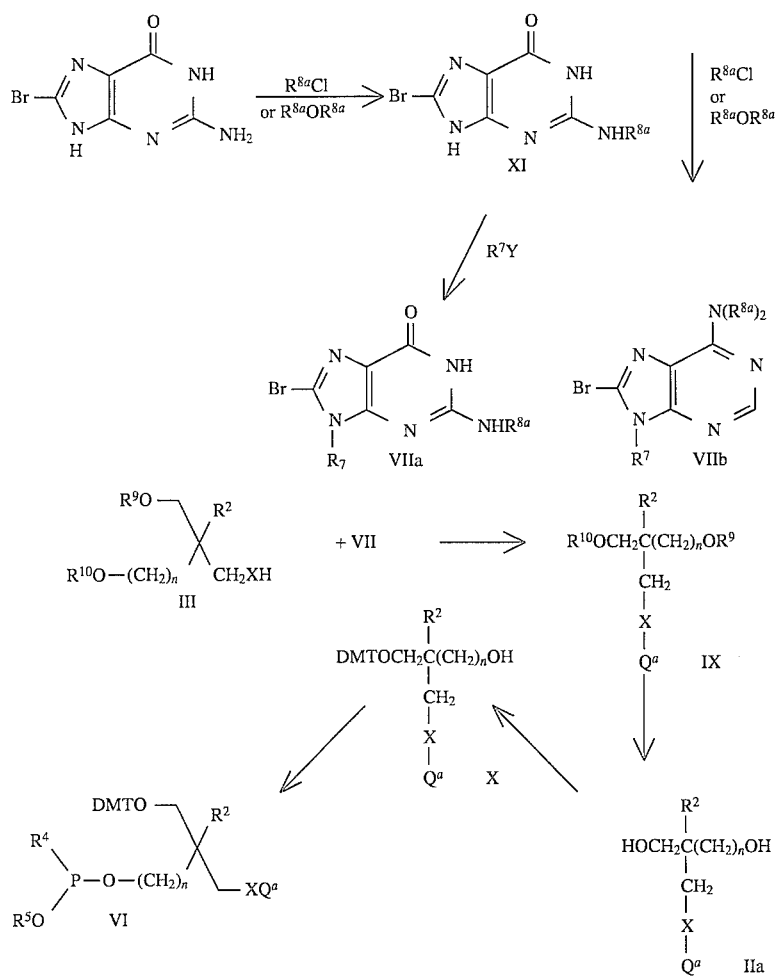

For guanosine analogs, commercially available 8-bromoguanine is acylated with an appropriate acid chloride or anhydride, preferably isobutyric anhydride, and alkylated with an appropriate lower-alkyl halide or sulfonate, preferably methyl iodide to produce a 2-acyl-9-alkyl-8-bromoguanine of formula VIIa. For adenosine analogs, commercially available adenine is alkylated with a lower-alkyl halide or sulfonate, preferably methyl iodide, brominated with molecular bromine at pH 4.0 in aqueous acetic acid-sodium acetate buffer and acylated with an acid chloride or anhydride, preferably benzoyl chloride to produce a 4,4-diacyl-9-alkyl-8-bromoadenine VIIb.

An 8-bromopurine (eg formulas VIIa or VIIb) is reacted with about 2 equivalents of the appropriate derivative of 1,ω-alkylenediol III in an inert solvent, preferably DMF. In the case where X is oxygen, it is preferred that $R^9$ and $R^{10}$ together form an isopropylidene residue; i.e. III is:

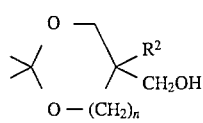 IIIa wherein n is 0 to 2, preferably 0 or 1 and it is preferred that the sodium salt of the alcohol be preformed by the addition of one equivalent of sodium hydride. The 8-bromopurine is then added to the alcoholate in the inert solvent. In the case where X is sulfur or $-NR^6-$ it is not necessary to protect the 1,ω-dihydroxyl functionality i.e. $R^9$ and $R^{10}$ may be hydrogen, and it is not necessary to preform the sulfur or nitrogen anions.

When $R^9$ and $R^{10}$ are other than hydrogen, it is necessary to convert them to hydrogen after condensation with the bromopurine by appropriate deprotection. Thus in the preferred case where X is oxygen and $R^9$ and $R^{10}$ together form a propylidene residue (IIIa), deprotection is accomplished by procedures well known in the art, for example using mild acid such as 0.25M $H_2SO_4$ in dioxane.

The compounds of formula IIa are prepared for incorporation into oligonucleotide sequences by protection of one hydroxyl with 4,4'dimethoxytrityl chloride according to procedures well-known in the art [see Schaller, Lerch and Khorana, J. Am. Chem. Soc. 85 3821–3827 (1963)] followed by reaction of the other hydroxyl with about 3 equivalents of 2-cyanoethyl N,N-diisopropylchlorophosphoramidite in THF also according to procedures known in the art [see Sinha et al. Tet. Lett. 24, 5843–5846 (1983)]. The compounds of formula VI that are preferred for further elaboration into sequences are the compounds in which $R^4$ is diisopropylamino and $R^5$ is β-cyanoethyl, but other "monomers" (VI) in which $R^4$ is chlorine, imidazole, 4-nitroimidazole, tetrazole, triazole, or other dilower-alkylamines and $R^5$ is methyl or 2,2,2-trichloroethyl may also be made by procedures known in the art [see Matteucci and Caruthers *Tet. Lett.* 22, 1859–1862 (1981) and Schaller et al. op. cit.]

The monomer unit VI and its precursor X are chiral compounds. The racemic mixture that arises from the synthesis as shown may be incorporated into oligomers, giving rise to diastersomeric sets of oligomers, which may themselves be separated if desired, or the enantiomers may be separated at the monomer stage. Common techniques that may be used if resolution is desired include chromatography on chiral media or the promotion of diasterosomeric esters of X with single enantiomers of chiral acids, separation of the diasteromers and hydrolysis to provide single enantiomers of X.

The compounds of formula VI are incorporated into oligonucleotide sequences by the substitution of a compound of formula VI for its corresponding dimethoxytrityl nucleoside phosphoramidite in standard procedures for the synthesis of oligonucleotides. Particularly preferred are solid phase syntheses such as those described by Matteucci and Caruthers [*J. Am. Chem. Soc.* 103, 3185–3191 (1981)] and Gait [*Oligonucleotide Synthesis: A Practical Approach,* ed. by M. J. Gait p. 35–81 IRL Press, Washington, D.C. 1984.]

The initial step in solid phase synthesis is attachment of a nucleoside to a solid support, preferably a controlled pore glass (CPG) support. The nucleoside is preferably attached to the CPG via a succinate linkage at the 3'-hydroxy position of the nucleoside. Other means of attaching nucleosides to solid supports are known and readily apparent to those of skill in the oligonucleotide synthesis art.

Following attachment of the first nucleoside to the solid support, chain elongation occurs via the sequential steps of removing the 5'-hydroxy protecting group, activating the 5'-hydroxy group in the presence of a phosphoramidite reagent, adding the desired nucleosides, capping the unreacted nucleosides and oxidizing the phosphorous linkage. The protecting group at the 5'-hydroxy position of the attached nucleosides is removed with acid, preferably trichloroacetic acid.

Activating reagents that can be used in accordance with this method are well known to those of skill in the art. Preferred activating reagents are tetrazole and activator gold (Beckman Instr. Inc., Palo Alto, Calif.).

The activation step occurs in the presence of the added nucleoside and a trityldiolcyanophosphine compound, which compound replaces the nucleoside phosphoramidite of coventional synthetic methods. Unreacted chains are terminated or capped with capping reagents such as acetic anhydride and N-methyl imidazole.

The labile trivalent phosphorus linkage is oxidized, preferably with iodine, to the stable, pentavalent phosphodiester linkage of the oligonucleotide.

After the desired oligonucleotide chain assembly is complete, the phosphate protecting groups are removed, the chains are separated from the solid support and the base protecting groups are removed by conventional methods. Gaits, supra at 67–70.

The compounds of the present invention are useful in treating mammals with hereditary disorders or diseases associated with altered genetic expression mechanisms. Examples of such diseases are viral infections such as HIV, cytomegalovirus, herpes simplex, hepatitis B, papilloma virus and picornavirus; cancers of the lung, colon, cervix, breast and ovary; inflammatory diseases; and diseases of the immune system such as acquired immunodeficiency syndrome (AIDS), hematological neoplasma and hyperproliferative disorders. Armstrong, supra at 89; Klausner, *Biotechnology* 8, 303 (1990).

Representative embodiments are disclosed in the examples which follow. it will be apparent to those skilled in the art that the examples may be readily modified by standard procedures to produce nucleotide oligomers of other lengths and with other sequences. Targets for synthesis will usually be chosen by substituting a residue of formula Va or Vb for guanosine or adenosine respectively in the

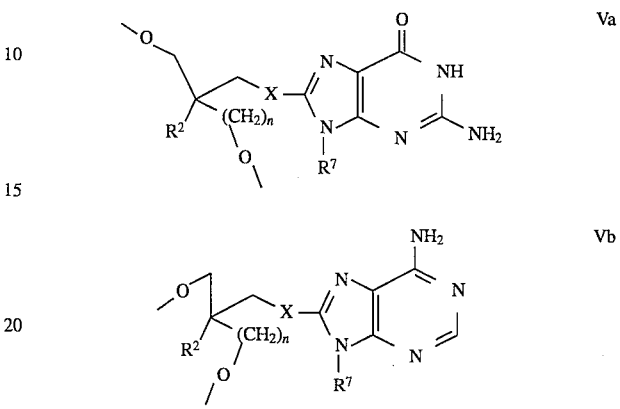

sequence which is to be protected from nuclease degradation or which is complementary to a sequence which is to be disabled.

The structures of the compounds of the invention were established by the mode of synthesis, by elemental analysis, and by infrared, nuclear magnetic resonance, and mass spectroscopy. The course of the reactions and identity and homogeneity of the products were assessed by thin layer chromatography or high pressure liquid chromatography. The abbreviation THF stands for tetrahydrofuran, DMF stands for N,N-dimethylformamide, iPr stands for isopropyl and DMT stands for 4,4'-dimethoxytrityl. Temperatures are given in degrees centigrade.

EXAMPLE 1

9-Methyladenine

A mixture of 43.2 g (0.23 mol) of adenine and 210 ml of 40% aqueous tetrabutylammonium hydroxide was stirred at room temperature for 30 minutes and 250 ml of methylene chloride was added. To this heterogenous mixture was added 40 ml (0.64 mol) of methyl iodide in 200 ml of methylene chloride. A further 450 ml of methylene chloride was added and the reaction was stirred vigorously for ten hours. The reaction was cooled to 10° and the liquid phase comprising methylene chloride and water was decanted from a milky precipitate which had formed. Methanol was added to the precipitate and the mixture warmed gently to 40°, cooled to 10° and the resulting granular solid filtered off. The solid was recrystallized from 350 ml of water to provide 20.9 g of 9-methyladenine.

EXAMPLE 2

8-Bromo-9-methyladenine

Fifteen grams (0.1 mol) of 9-methyladenine of Example 1 was dissolved in 1.5 liters of buffer prepared from 30.8 g of sodium acetate, 1.4 liters of water and sufficient acetic acid to provide a pH of 4.0. To this solution was added dropwise 25 ml of bromine in 2 liters of water over a period of two hours. The reaction was stirred a further two hours and the resulting solid filtered off and rinsed with the water.

The solid was air dried and warmed to about 50° in about 80 ml of methanol, stripped to a hazy suspension and filtered. The precipitate after rinsing with water and drying at 40° under vacuum overnight weighed 15.6 g. The filtrate was stripped of methanol and a further 1.6 g was collected. The combined solids were triturated in about 100 ml of acetone for three hours and then allowed to sit overnight. The resulting precipitate was filtered and washed with acetone to yield 13.3 g after drying at 40° on a vacuum pump overnight.

EXAMPLE 3

6-(Dibenzoylamino)-8-bromo-9-methyl-purine

Thirty-four grams (0.15 mol) of 6-amino-8-bromo-9-methylpurine prepared according to the procedure of Example 2 was dissolved in 100 ml of anhydrous pyridine and stripped. The residue was redissolved in 800 ml of pyridine, cooled to 0° to 10° and 80 ml (0.69 mol) of benzoylchloride was added dropwise over the course of two hours. The reaction was stirred at 15 degrees for a further four hours and decanted from a small amount of insoluble residue into ice water saturated with sodium bicarbonate. The product was extracted into about 2.5 liters of methylene chloride, dried over magnesium sulfate, filtered and stripped. The residue was stripped twice with toluene to remove traces of pyridine, dissolved in about 150 ml of ethyl acetate and seeded. After crystallization had begun a further 70 ml of ethyl acetate was added and after two hours the mixture was chilled and about 34 g of product was collected by filtration. The product was dissolved in about 500 ml of methylene chloride and filtered through about 400 ml of silica gel to yield, after stripping, 21.5 g of 6-(dibenzoylamino)-8-bromo-9-methyl-purine.

EXAMPLE 4

6-(Benzoylamino)-9-methyl-8-[5-(2,2,5-trimethyl-1,3-dioxanyl)methoxy]purine

To a suspension of 1.5 g (37.5 mmol) of 60% sodium hydride in oil was added 5.0 g (31 mmol) of 2,2,5-trimethyl-5-[1,3]dioxanemethanol prepared according to the procedure of V. W. Gash, J. Org. Chem. 37, 2197–2201 (1972). The mixture was stirred at 30° for about one hour and 12 g (27 mmol) of 8-bromo-6-(dibenzoylamino)-9-methyl-purine of Example 3 was added with stirring. After 90 min TLC showed mainly starting material so a further 18 mmol of the sodium salt of the hydroxymethyldioxane was added. The mixture was stirred at 35° C. for twelve hours. TLC showed some remaining starting material so a further 8 mmol of sodium salt was added and the reaction stirred for a further four hours at 35°. The reaction was cooled to 10° and dripped into a mixture of ice water and ethyl acetate. The layers were separated and the aqueous layer comprising about 400 ml was extracted three times with 500 ml of ethyl acetate. The ethyl acetate washings were combined, dried over magnesium sulfate, filtered and stripped on the rotovap with a vacuum pump to yield 18.4 g of thick yellow oil that still contained mineral oil from the sodium hydride. The 18.4 g of oil was dissolved in 400 ml of methylene chloride containing 1 ml of triethylamine and applied to 250 ml of silica gel. After some impurities had rinsed through, the product was eluted with 10% methanol in dichloromethane containing 0.2% triethylamine. Eight grams of yellow solid product and 1.4 g of a light yellow gum consisting of product and some DMF were obtained.

EXAMPLE 5

6-Benzoylamino-8-[3-hydroxy-2-(hydroxymethyl)-2-methylpropoxy]-9-methylpurine

The 8 g of yellow solid of the previous example was dissolved in 60 ml of dioxane and 60 ml of 0.25 molar sulfuric acid was added. The reaction was stirred at room temperature for two hours and then allowed to stand at room temperature for five days. The pH was adjusted to 7.5 with triethylamine and the reaction stripped at 35°. The reaction was stripped twice with toluene to remove remaining water. The 11 g of residue was dissolved in 150 ml of methylene chloride and chromatographed on 445 ml of silica gel eluting with a gradient from 1 to 10% methanol in dichloromethane. The product which came off with 10% methanol in dichloromethane was recrystallized from ethyl acetate to provide 5.25 g of 6-(benzoylamino)-8-[3-hydroxy-2-(hydroxymethyl)-2-methylpropoxy]-9-methylpurine.

EXAMPLE 6

Compound X: $R_2$=methyl, X=oxygen, $Q^a$=$Q^{a1}$, $R_7$=methyl

A solution of 500 mg (13.5 mmol) of the diol from Example 5 in 20 ml of pyridine was stirred with 500 mg (14 mmol) of dimethoxytrityl chloride at room temperature for 18 hours and 1 ml of methanol was added. The reaction was stirred another six hours and poured into saturated aqueous bicarbonate. The product was extracted three times with methylene chloride, washed with water, dried over sodium sulfate, filtered and stripped twice with toluene. The resulting glass was dissolved in 5% methanol in methylene chloride containing about 0.1% triethylamine and chromatographed on silica gel eluting with a gradient from 1 to 10% methanol in methylene chloride. The product came off at about 2 to 5% methanol in methylene chloride containing about 0.1% triethylamine. The resulting foam was dissolved in a small volume of methanol then two drops of triethylamine and about 10 ml of water was added and the resulting solid filtered off to yield 530 mg of product.

EXAMPLE 7

Compound VI: $R_2$=methyl, $R_4$=diisopropylamino, $R_5$=cyanoethyl, X=oxygen, $Q^{a=Qa1}$ and $R_7$=methyl The condensation of the product of example 6 with phosphoramidite was carried out as described by Sinha et al. Tett. Letters 24, 5843–5846 (1983). The reaction mixture was placed directly on a silica gel column which had been equilibrated with nitrogen-saturated methyl acetate containing 0.5% triethylamine. Upon elution with the above mixture, 600 mg of product containing a small amount of starting material was obtained. It was rechromatographed on silica gel with nitrogen-saturated 20% ethyl acetate in methylene chloride containing 0.5% triethylamine to obtain 100 mg of pure product.

EXAMPLES 8 TO 12

The oligomers of examples 8 to 12 were synthesized using standard procedures on an Applied Biosystems model 380B DNA synthesizer with modifications as outlined. In all successful couplings a 5-fold to 10-fold excess of the acyclic monomer from example 7 was used. In the following table, A* indicates a residue of structure:

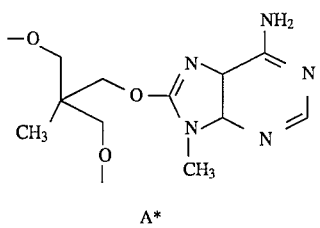

A*

The purity of the oligomers was assessed by reverse phase and ion exchange HPLC.

TABLE 1

| Example | Structure |
| --- | --- |
| 8 | 5'-CCT TCT CA*G TCG GA*C-3' |
| 9 | 5-AAC GTT GAG GGG CA*T-3' |
| 10 | 5'AAA AAA AAA AAA AA*A-3' |
| 11 | 5'-AAA AAA AAA AAA A*AA-3' |
| 12 | 5'-A*A*A* A*A*A* A*A*A* A-3' |

EXAMPLE 13

6-(Benzoylamino)-9-methyl-
8-[5-(2,2-dimethyl-1,3-dioxanyl)methoxy]purine,
IX: $R_2$=H, $R_9$+$R_{10}$=isopropylidene, X=O, $Q^a$=$Q^{a1}$,
$R_7$=$CH_3$ By a procedure analogous to that of example 4, 4.17 g of 6-(benzoylamino)-9-methyl-8-[5-(2,2-dimethyl-1,3-dioxanyl)methoxy]purine was synthesized from 7.4 g (17 mmol) of 8-bromo-6-(dibenzoylamino)-9-methylpurine of example 3 and 5.16 g (35 mmol) of 2,2-dimethyl-5-hydroxymethyl-1,3-dioxane.

EXAMPLE 14

6-(Benzoylamino)-8-[3-hydroxy-
2-(hydroxymethyl)propoxy]-9-methylpurine, IIa:
$R_2$=H, X=0, $Q^a$=$Q^{a1}$, $R_7$=$CH_3$ By a process analogous to that of example 5, 1.5 g of 6-(benzoylamino)-8-[3-hydroxy-2-(hydroxymethyl)propoxy]-9-methylpurine was synthesized from 4.1 g of the isopropylidene-protected diol of example 13. The product was recrystallized from methanol/ether; m.p. 151°–153° as the monohydrate.

EXAMPLE 15

N-(8-Bromo-6,7-dihydro-6-oxo-3H-purin-2-yl
-2-methylpropanamide, XI: $R^{8a}$=$(CH_3)_2CHCO$—

A suspension of 3.45 g (15 mmol) of 8-bromoguanine in 100 ml of isobutyric anhydride was heated at 150° under nitrogen for 4 hours, cooled and 3.6 g of product filtered off. The product was washed with ether and used in example 16.

EXAMPLE 16

N-(8-Bromo-6,9-dihydro-9-methyl-6-oxo-3H-purin-2-yl)-2-methylpropanamide, VIIa: $R^7$=$CH_3$, $R^{8a}$=$(CH_3)_2CHCO$—

By a process analogous to that of example 1, 3.0 g (10 mmol) of N-(8-bromo-6,7-dihydro-6-oxo-3H-purin-2-yl)-2-methylpropanamide of example 15 was converted to 610 mg of N-(8 -bromo-6, 9 -dihydro-9-methyl-6-oxo-1H-purin-2-yl)-2-methylpropanamide m.p. 294° (d) from chloroform/hexane.

EXAMPLE 17

N-(8-bromo-6,9-dihydro-6-oxo-9-propyl-
3H-purin-2-yl)-2-methylpropanamide, VIIa:
$R^7$=n-propyl, $R^{8a}$=$(CH_3)_2CHCO$—

By a process analogous to that of example 16, it is contemplated that N-(8-bromo-6, 9-dihydro-6-oxo-9-propyl -3H-purin-2-yl)-2-methylpropanamide may be synthesized from N-(8-bromo-6,7-dihydro-6-oxo-3H-purin-2-yl)-2 -methylpropanamide of example 15 substituting n-propyl iodide for methyl iodide.

EXAMPLE 18

Compound IIa: $R_2$=H, X=$NCH_3$, $Q^a$=$Q^{a1}$, $R^7$=$CH_3$

By a process analogous to that of example 4, it is contemplated that compound IIa above may be obtained from the bromopurine of example 3 and 2-[(methylamino)methyl]-1,3-propanediol which is obtained by monomethylation of 2-methylamino-1,3-propanediol.

EXAMPLE 19

Compound IIa: $R^2$=H, X=S, $Q^a$=$Q^{a1}$, $R^7$=$CH_3$

By a process analogous to that of example 4, it is contemplated that compound IIa above, may be obtained from the bromopurine of example 3 and 5-mercaptomethyl-2,2-dimethyl-1,3-dioxane.

It is contemplated that 5-mercaptomethyl-2,2-dimethyl-1,3-dioxane may be synthesized from the corresponding alcohol (see example 4) by iodination with iodine/triphenyl phosphine followed by displacement with sodium sulfide.

Representative oligomers of the invention were tested for nuclease inhibition, for hybridization, and for inhibition of mRNA translation.

Nuclease Stability

Antisense oligonucleotides were evaluated (and compared against unmodified oligonucleotides) for their stability in the presence of 10% (v/v) fetal bovine serum (FBS) in RPMI 1640 cell culture media containing 20 mM HEPES buffer (complete media). FBS and human serum are known to contain a 3'→5' exonuclease activity. This represents the only nuclease activity we have been able to detect in FBS, human serum, and human plasma. Oligonucleotide samples were incubated at 37° C. in complete media over a six hour time period and the amount of parent compound determined using an HPLC-based procedure.

The compound of example 10 elutes as two major peaks on a GEN-PAK FAX (Waters) anion exchange column. These two peaks represent the expected R and S forms of the molecule. After six hours in the presence of 10% FBS, a stable reaction product was observed for example 10. In contrast to the degradation of d(A)$_{15}$, the progression of the FBS associated 3'→5' exonuclease activity is halted at the acyclo residue.

Measurement of DNA/DNA Duplex Melting Temperatures

Oligonucleotide concentrations were determined spectrophotometrically utilizing extinction coefficients at 260 nm calculated using the method and values presented by Warsaw, Cantor, and Tinoco [CRC Handbook of Biochemistry and Molecular Biology (G. D. Fasman, editor) 1:589 (1975)]. Equimolar concentrations of oligonucleotide and its complementary sequence were combined (in 0.1 mM EDTA, 10 mM sodium phosphate, 0.1M NaCl, pH 7.0) heated to 80° C. and allowed to cool slowly at room temperature. Samples were allowed to remain at room temperature for about 2.5 hours. Samples were then heated at a rate of 0.5° C./min (25° C.–75° C.) in a thermostatically controlled heat block and absorbance monitored at 260 nm using a Perkin Elmer Lambda 4C UV spectrophotometer. $A_{260}$ measurements were taken every 15 seconds. Data were transferred to a DEC VAX for data analysis using RS/1 data analysis software. Tm's were determined from a plot of dA260/dT vs. temperature. The Tm is that temperature at which dA260/dT is maximum. The results are presented in Table 2.

TABLE 2

| Oligomer ID | Sequence 5'→3' | TM(°C.) | Delta Tm |
|---|---|---|---|
| Control | AAA AAA AAA AAA AAA | 42.0 | — |
| ex 10 | AAA AAA AAA AAA AA*A | 40.0 | −2.0 |
| ex 11 | AAA AAA AAA AAA A*AA | 38.0 | −4.0 |
| Control | CCT TCT CAG TCG GAC | 64.6 | — |
| ex 8 | CCT TCT CA*G TCG GA*C | 58.1 | −6.5 |
| Control | AAC GTT GAG GGG GAT | 64.3 | — |
| ex 9 | AAC GTT GAG GGG GA*T | 64.2 | −0.1 |
| ex 12 | A*A*A* A*A*A* A*A*A* A | — | — |

Total Strand Concentration = 9.0 uM
A* = 9-methyl-8-acycloadenosine

Example 12 (a diastereomeric mixture) and its complementary strand were annealed overnight at 4° C. prior to melting and the rate of temperature increase set at 0.1° C./min over the temperature range of 18° C.–38° C. with A260 measurements taken every 30 sec. The thermal denaturation profile for this duplex was not very sharp with more than one dA260/dT maximum observed; however, it would indicate that hybridization did occur.

Inhibition of Rabbit Alpha Globin mRNA Translation

Cell free translation of rabbit globin mRNA (Bethesda Res. Labs, Gaithersburg, Md.) +/−6.5 units/5 uL E. coli RNase H (Boehringer Mannheim, Indianapolis, Ind.) with the addition of antisense oligonucleotides was carried out using rabbit reticulocyte lysate (Promega, Madison, Wis.) in a total volume of 50 uL. 25 uCi of 35S-methionine (New England Nuclear, Boston, Mass.) was added to each translation reaction. Translations were incubated at 30° C. for 10 min., after which time samples were snap frozen on dry ice. Alpha and beta globin chains were separated using SDS-polyacrylamide gel electrophoresis. The 15 cm gels were prepared using electrophoresis buffer (0.1M sodium phosphate, pH 7.2 containing 1.0 g of SDS/L) and contained 12.5% acrylamide and 0.6% bisacrylamide. Aliquots (1 uL) of translation reactions were diluted with 11 uL of loading buffer consisting of electrophoresis buffer, 1.1% 2-mercaptoethanol, 2.5% glycerol and bromphenol blue. Samples were denatured by heating to 100° C. for 3 min. before loading onto gels. The gels were run for 18 hours at 30 mAMP. After electrophoresis, gels were stained with coomassie blue, dried and autoradiographed at −70° C. for 16 hours.

Quantitation of the effects of alpha globin directed antisense oligonucleotides on the synthesis of alpha globin was done by scanning the autoradiographs using an Ultrascan XL laser densitometer (LKB/Bromma) linked to an AT&T PC6300 computer. Data were collected, displayed and integrated with the Gelscan XL data analysis software package (LKB/Bromma). Effects of oligomers on protein synthesis were expressed as a percent of control alpha globin synthesis. The oligomer of example 8 inhibited translation to 74±10% of control in the absence of RNase H and 84±5% in the presence of RNase H at an oligomer strand concentration of 30 μM.

The pharmaceutical compositions of the present invention include one or more of the compounds of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone. sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

---

---

We claim:

1. A compound of the formula:

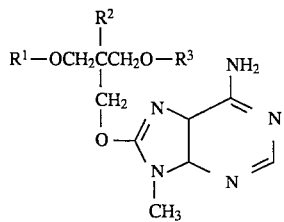

wherein $R^1$ is hydrogen, or a blocking group that is compatible with oligonucleotide synthesis;

$R^2$ is hydrogen or methyl;

$R^3$ is hydrogen or —$P(R^4)OR^5$;

$R^4$ is chloro, 4-nitroimidazolyl, imidazolyl, tetrazolyl, triazolyl or di(lower-alkyl)amino-;

$R^5$ is methyl, 2-cyanoethyl or 2,2,2-trichloroethyl.

2. A compound according to claim 1, having the formula

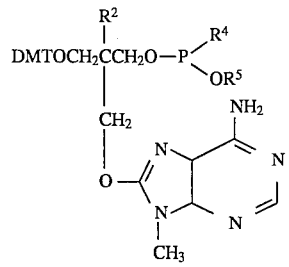

3. A compound according to claim 2 wherein $R^5$ is cyanoethyl, and $R^4$ is diisopropylamino.

4. A compound comprising an oligonucleotide sequence of from about 6 to about 200 bases in which one or more nucleosides at the 3' terminus of said oligonucleotide are replaced by a residue of formula

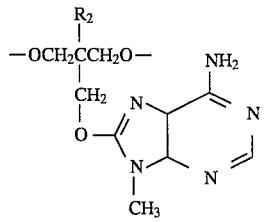

wherein

R² is hydrogen or methyl.

5. A compound according to claim 4 wherein said oligonucleotide sequence comprises from about 12 to about 24 bases.

6. A compound according to claim 5 wherein said oligonucleotide sequence comprises 15 bases.

7. A compound of formula

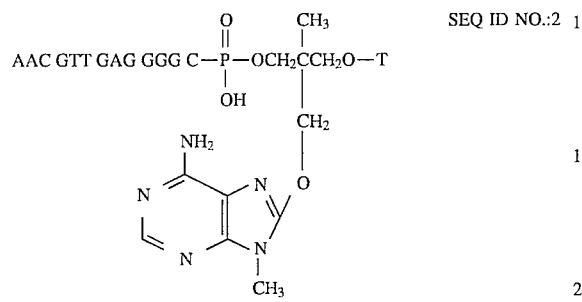
SEQ ID NO.:2 according to claim 6.

8. A method of inhibiting nuclease degradation of an oligonucleotide comprising replacing one or more nucleosides at the 3' terminus of said oligonucleotide by a residue of formula

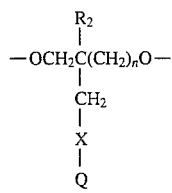

wherein $R_2$ is hydrogen, nitro, lower-alkyl amino, diloweralkyl amino or methyl;

X is oxygen, sulfur or $-NR^6$;

n is 0 to 2;

$R^6$ is hydrogen or lower-alkyl;

Q is chosen from the group consisting of

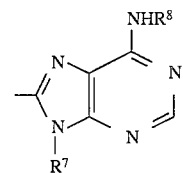

and

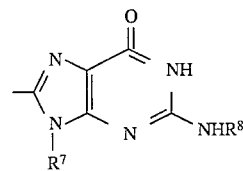

$R^7$ is lower-alkyl or loweralkyloxy ethylene; and $R^8$ is hydrogen, benzoyl, anisoyl, or lower-alkyl carbonyl.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH:15
        ( B ) TYPE:Nucleic Acid
        ( C ) STRANDEDNESS:single
        ( D ) TOPOLOGY:linear ( i i ) MOLECULE TYPE:Nucleic Acid
        ( A ) DESCRIPTION:

( i v ) ANTI-SENSE:yes ( v i ) ORIGINAL SOURCE:synthesized ( i x ) FEATURE:
        ( B ) LOCATION:8 & 14
        ( D ) OTHER INFORMATION:8-[2,2- bis(methoxymethyl propoxy]-9-methyladenosine ( x i ) SEQUENCE DESCRIPTION: SEQ ID NO:1:

CCTTCTCNGT CGGNC 15

( 2 ) INFORMATION FOR SEQ ID NO:2:

( i ) SEQUENCE CHARACTERISTICS:
        ( A ) LENGTH:15
        ( B ) TYPE:Nucleic Acid
        ( C ) STRANDEDNESS:single
        ( D ) TOPOLOGY:linear ( i i ) MOLECULE TYPE:Nucleic Acid
        ( A ) DESCRIPTION:

( i v ) ANTI-SENSE:yes ( v i ) ORIGINAL SOURCE:synthesized ( i x ) FEATURE:
        ( B ) LOCATION:14
        ( D ) OTHER INFORMATION:8-[2,2- bis(methoxymethyl propoxy]-9-methyladenosine ( x i ) SEQUENCE DESCRIPTION: SEQ ID NO:2:

AACGTTGAGG GGCNT 15

( 2 ) INFORMATION FOR SEQ ID NO:3:

( i ) SEQUENCE CHARACTERISTICS:
        ( A ) LENGTH:15
        ( B ) TYPE:Nucleic Acid
        ( C ) STRANDEDNESS:single
        ( D ) TOPOLOGY:linear ( i i ) MOLECULE TYPE:Nucleic Acid
        ( A ) DESCRIPTION:

( i v ) ANTI-SENSE:yes ( v i ) ORIGINAL SOURCE:synthesized ( i x ) FEATURE:
    ( B ) LOCATION:14
    ( D ) OTHER INFORMATION: 8-[2,2- bis(methoxymethyl propoxy]-9-methyladenosine ( x i ) SEQUENCE DESCRIPTION: SEQ ID NO:3:

A A A A A A A A A    A A A N A    1 5

( 2 ) INFORMATION FOR SEQ ID NO:4:

( i ) SEQUENCE CHARACTERISTICS:
    ( A ) LENGTH:15
    ( B ) TYPE:Nucleic Acid
    ( C ) STRANDEDNESS:single
    ( D ) TOPOLOGY:linear ( i i ) MOLECULE TYPE:Nucleic Acid
    ( A ) DESCRIPTION:

( i v ) ANTI-SENSE:yes ( v i ) ORIGINAL SOURCE:synthesized ( i x ) FEATURE:
    ( B ) LOCATION:13
    ( D ) OTHER INFORMATION:8-[2,2- bis(methoxymethyl propoxy]-9-methyladenosine ( x i ) SEQUENCE DESCRIPTION: SEQ ID NO:4:

A A A A A A A A A    A A N A A    1 5

( 2 ) INFORMATION FOR SEQ ID NO:5:

( i ) SEQUENCE CHARACTERISTICS:
    ( A ) LENGTH:10
    ( B ) TYPE:Nucleic Acid
    ( C ) STRANDEDNESS:single
    ( D ) TOPOLOGY:linear ( i i ) MOLECULE TYPE:Nucleic Acid
    ( A ) DESCRIPTION:

( i v ) ANTI-SENSE:yes ( v i ) ORIGINAL SOURCE:synthesized ( i x ) FEATURE:
    ( B ) LOCATION:1-9
    ( D ) OTHER INFORMATION:8-[2,2- bis(methoxymethyl propoxy]-9-methyladenosine ( x i ) SEQUENCE DESCRIPTION: SEQ ID NO:5:

N N N N N N N N N A    1 0

( 2 ) INFORMATION FOR SEQ ID NO:6:

( i ) SEQUENCE CHARACTERISTICS:
    ( A ) LENGTH:15
    ( B ) TYPE:Nucleic Acid
    ( C ) STRANDEDNESS:single
    ( D ) TOPOLOGY:linear ( i i ) MOLECULE TYPE:Nucleic Acid
    ( A ) DESCRIPTION:

( i v ) ANTI-SENSE:no ( v i ) ORIGINAL SOURCE:synthesized ( x i ) SEQUENCE DESCRIPTION: SEQ ID NO:6:

A A A A A A A A A    A A A A A    1 5

( 2 ) INFORMATION FOR SEQ ID NO:7:

( i ) SEQUENCE CHARACTERISTICS:
        ( A ) LENGTH:15
        ( B ) TYPE:Nucleic Acid
        ( C ) STRANDEDNESS:single
        ( D ) TOPOLOGY:linear ( i i ) MOLECULE TYPE:Nucleic Acid
        ( A ) DESCRIPTION:

( i v ) ANTI-SENSE:no ( v i ) ORIGINAL SOURCE:synthesized ( x i ) SEQUENCE DESCRIPTION: SEQ ID NO:7:

CCTTCTCAGT CGGAC 15

( 2 ) INFORMATION FOR SEQ ID NO:8:

( i ) SEQUENCE CHARACTERISTICS:
        ( A ) LENGTH:15
        ( B ) TYPE:Nucleic Acid
        ( C ) STRANDEDNESS:single
        ( D ) TOPOLOGY:linear ( i i ) MOLECULE TYPE:Nucleic Acid
        ( A ) DESCRIPTION:

( i v ) ANTI-SENSE:no ( v i ) ORIGINAL SOURCE:synthesized ( x i ) SEQUENCE DESCRIPTION: SEQ ID NO:8:

AACGTTGAGG GGGAT 15